United States Patent
Liang et al.

(10) Patent No.: US 11,031,107 B2
(45) Date of Patent: Jun. 8, 2021

(54) EXTRACTING PATIENT INFORMATION FROM AN ELECTRONIC MEDICAL RECORD

(71) Applicant: International Business Machines Corporation, Armonk, NY (US)

(72) Inventors: Jennifer J. Liang, New York, NY (US); Tejaswini Pedapati, New York, NY (US); John M. Prager, Pomona, NY (US)

(73) Assignee: International Business Machines Corporation, Armonk, NY (US)

( * ) Notice: Subject to any disclaimer, the term of this patent is extended or adjusted under 35 U.S.C. 154(b) by 925 days.

(21) Appl. No.: 15/403,363

(22) Filed: Jan. 11, 2017

(65) Prior Publication Data

US 2018/0196920 A1    Jul. 12, 2018

(51) Int. Cl.
*G06F 16/2458* (2019.01)
*G16H 10/60* (2018.01)
(Continued)

(52) U.S. Cl.
CPC ......... *G16H 10/60* (2018.01); *G06F 16/2465* (2019.01); *G16H 10/20* (2018.01);
(Continued)

(58) Field of Classification Search
CPC ............... G06F 16/2428; G06F 16/532; G06F 16/2423; G06F 16/2465
See application file for complete search history.

(56) References Cited

U.S. PATENT DOCUMENTS 7,711,580 B1    5/2010   Hudson
8,239,216 B2    8/2012   McCallie, Jr. et al.
(Continued)

FOREIGN PATENT DOCUMENTS

WO    WO 2014/169124 A1    10/2014

OTHER PUBLICATIONS

"Resource and Patient Management System—Electronic Health Record (RPMS-EHR), User Manual", 2007, Indian Health Services, Albuquerque, New Mexico. (Year: 2007).*
(Continued)

*Primary Examiner* — Sheryl L Holland
(74) *Attorney, Agent, or Firm* — Stephen R. Tkacs; Stephen J. Walder, Jr.; Ryan G. Lewis

(57) ABSTRACT

A mechanism is provided in a data processing system comprising at least one processor and at least one memory comprising instructions, which are executed by the at least one processor and configure the processor to implement a patient information extractor. The patient information extractor receives a query specification for executing a query on a patient electronic medical record (EMR). The query specification provides parameters indicating a methodology for extracting search results from the patient EMR. The patient information extractor retrieves the patient EMR from a patient registry. The patient information extractor automatically executes the query specification on the retrieved patient EMR to thereby extract the search results from the patient EMR in accordance with the parameters of the query specification. The patient information extractor automatically processes the extracted search results to generate a patient indicator value. The patient indicator value represents an answer to a question about the patient. A patient evaluation operation is performed based on the patient indicator value.

20 Claims, 4 Drawing Sheets

(51) Int. Cl.
*G16H 10/20* (2018.01)
*G16H 50/20* (2018.01)
*G06F 16/242* (2019.01)

(52) U.S. Cl.
CPC ...... *G06F 16/2423* (2019.01); *G06F 16/2428* (2019.01); *G16H 50/20* (2018.01)

(56) References Cited

U.S. PATENT DOCUMENTS

| | | | |
|---|---|---|---|
| 8,275,803 | B2 | 9/2012 | Brown et al. |
| 2004/0243545 | A1 | 12/2004 | Boone et al. |
| 2009/0006132 | A1 | 1/2009 | Avinash et al. |
| 2009/0287678 | A1 | 11/2009 | Brown et al. |
| 2011/0066587 | A1 | 3/2011 | Ferrucci et al. |
| 2011/0125734 | A1 | 5/2011 | Duboue et al. |
| 2012/0078062 | A1* | 3/2012 | Bagchi ............... A61B 5/00 600/300 |
| 2012/0246105 | A1* | 9/2012 | James ................ G16H 40/20 706/47 |
| 2013/0007055 | A1 | 1/2013 | Brown et al. |
| 2013/0018652 | A1 | 1/2013 | Ferrucci et al. |
| 2013/0066886 | A1 | 3/2013 | Bagchi et al. |
| 2016/0019299 | A1 | 1/2016 | Boloor et al. |
| 2016/0110523 | A1* | 4/2016 | Francois ............. G06Q 50/24 705/2 |
| 2016/0232298 | A1* | 8/2016 | Campbell ............ G16H 10/60 |

OTHER PUBLICATIONS

Holzinger et al., "Disease-disease relationships for rheumatic diseases", 2012, IEEE. (Year: 2102).*

Hammer et al., "Template-Based Wrappers in the TSIMMIS System", 1997, Stanford University. (Year: 1997).*

"A Method and System for Automatically Selecting Patient Cohorts from Electronic Health Records using Flexible Search and an Automatic Longitudinal Patient Record formation", Disclosed Anonymously, An IP.com Prior Art Database Technical Disclosure, IP.com No. IPCOM000241430D, Apr. 25, 2015, 6 pages.

"Clinical Content Categorization from Electronic Medical Records (EMRs) without Assignment of Codes", Disclosed Anonymously, An IP.com Prior Art Database Technical Disclosure, IP.com No. IPCOM000245141D, Feb. 12, 2016, 15 pages.

"Latent semantic analysis", Wikipedia, https://en.wikipedia.org/wiki/Latent_semantic_analysis, retrieved from the internet Jun. 2, 2016, 13 pages.

"MetaMap—A Tool for Recognizing UMLS Concepts in Text", U.S. National Library of Medicine, National Institutes of Health, https://metamap.nlm.nih.gov, retrieved from the internet Jun. 2, 2016, 2 pages.

"Unified Medical Language System (UMLS)", U.S. National Library of Medicine, National Institutes of Health, https://www.nlm.nih.gov/research/umls, retrieved from the internet Jun. 2, 2016, 2 pages.

Barkhuysen, Pashiera et al., "Is the quality of data in an electronic medical record sufficient for assessing the quality of primary care?", American Medical Informatics Association, vol. 21, No. 4, Jul. 2014, pp. 692-698.

High, Rob, "The Era of Cognitive Systems: An Inside Look at IBM Watson and How it Works", IBM Corporation, Redbooks, Dec. 12, 2012, 16 pages.

Limsopatham, Nut, "A Framework for Enhancing the Query and Medical Record Representations for Patient Search", ACM, Doctoral Abstract, ACM SIGIR Forum, vol. 49, No. 1, Jun. 2015, pp. 68-69.

McCord, M.C. et al., "Deep parsing in Watson", IBM J. Res. & Dev. vol. 56 No. 3/4 Paper 3, May/Jul. 2012, pp. 3:1-3:15.

Sahoo, Satya S. et al., "Trial Prospector: Matching Patients with Cancer Research Studies Using an Automated and Scalable Approach", Cancer Informatics, 2014: 13, Oct. 4, 2014, pp. 157-166.

Yuan, Michael J., "Watson and healthcare, How natural language processing and semantic search could revolutionize clinical decision support", IBM developerWorks, IBM Corporation, Apr. 12, 2011, 14 pages.

* cited by examiner

*FIG. 5*

```
Query Spec:
    {
        "name":"Oophorectomy",
        "column":1,
        "searchResultProcessorType":"SpecificIndicator",
        "startDate":"24/5/2007",   ⎫
        "endDate":"24/5/2007",     ⎬ DATE RESTRICTION 501
        "QSBs":[
            {
                "QSB":{
                    "name":"Bilateral salpingooophorectomy",
                    "searchTerm":"Bilateral salpingo-oophorectomy OR bilateral oophorectomy",
                    "value":"2"
                }
            },            BOTH SIDES 511
            {
                "QSB":{
                    "name":"Right OR left salpingooophorectomy",
                    "searchTerm":"Right salpingo-oophorectomy OR left salpingo-oophorectomy",
                    "value":"1"
                }
            },            LEFT OR RIGHT 512
            {
                "QSB":{
                    "name":"None",
                    "searchTerm":"None",
                    "default":true,
                    "value":"0"
                }
            }             NONE 513
        ],
        "notetype to require":[
            "operativenote",
            "ednote",
            "consultnote",
            "procedurenote"
        ],
        "LSE to use":[
            "SemanticMatch"
        ],
        "MinimumCount":1
    }
```

QSB 502
QSB 503
QSB 504
NOTE TYPE 505

EXTRACTING PATIENT INFORMATION FROM AN ELECTRONIC MEDICAL RECORD

BACKGROUND

The present application relates generally to an improved data processing apparatus and method and more specifically to mechanisms for extracting patient information from an electronic medical record (EMR).

A decision support system (DSS) is a computer-based information system that supports business or organizational decision-making activities. DSSs serve the management, operations, and planning levels of an organization (usually mid and higher management) and help people make decisions about problems that may be rapidly changing and not easily specified in advance—i.e. Unstructured and Semi-Structured decision problems. Decision support systems can be either fully computerized, human-powered or a combination of both.

A clinical decision support system (CDSS) is a health information technology system that is designed to provide physicians and other health professionals with clinical decision support (CDS), that is, assistance with clinical decision-making tasks. CDSSs constitute a major topic in artificial intelligence in medicine.

A common purpose of modern CDSS is to assist clinicians at the point of care. This means that clinicians interact with a CDSS to help to analyze, and reach a diagnosis based on, patient data. In the early days, CDSSs were conceived of as being used to literally make decisions for the clinician. The clinician would input the information and wait for the CDSS to output the "right" choice and the clinician would simply act on that output. However, the modern methodology of using CDSSs to assist means that the clinician interacts with the CDSS, utilizing both their own knowledge and the CDSS, to make a better analysis of the patient's data than either human or CDSS could make on their own. Typically, a CDSS makes suggestions for the clinician to look through, and the clinician is expected to pick out useful information from the presented results and discount erroneous CDSS suggestions.

An example of how a CDSS might be used by a clinician is a specific type of Clinical Decision Support System, a DDSS (Diagnosis Decision Support Systems). A DDSS requests some of the patients data and in response, proposes a set of appropriate diagnoses. The doctor then takes the output of the DDSS and determines which diagnoses might be relevant and which are not, and if necessary orders further tests to narrow down the diagnosis.

Another important classification of a CDSS is based on the timing of its use. Doctors use these systems at point of care to help them as they are dealing with a patient, with the timing of use being either pre-diagnosis, during diagnosis, or post diagnosis. Pre-diagnosis CDSS systems are used to help the physician prepare the diagnoses. CDSS used during diagnosis help review and filter the physician's preliminary diagnostic choices to improve their final results. Post-diagnosis CDSS systems are used to mine data to derive connections between patients and their past medical history and clinical research to predict future events. It has been claimed that decision support will begin to replace clinicians in common tasks in the future.

Another approach, used by the National Health Service in England, is to use a DDSS (either operated by the patient or by a phone operative who is not medically-trained) to triage medical conditions out of hours by suggesting a suitable next step to the patient (e.g., call an ambulance, or see a general practitioner on the next working day). The suggestion, which may be disregarded by either the patient or the phone operative if common sense or caution suggests otherwise, is based on the known information and an implicit conclusion about what the worst-case diagnosis is likely to be.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising at least one processor and at least one memory, the at least one memory comprising instructions which are executed by the at least one processor and configure the processor to implement a patient information extractor. The method comprises receiving, by the patient information extractor, a query specification for executing a query on a patient electronic medical record (EMR). The query specification provides parameters indicating a methodology for extracting search results from the patient EMR. The method further comprises retrieving, by the patient information extractor, the patient EMR from a patient registry. The method further comprises automatically executing, by the patient information extractor, the query specification on the retrieved patient EMR to thereby extract the search results from the patient EMR in accordance with the parameters of the query specification. The method further comprises automatically processing, by the patient information extractor, the extracted search results to generate a patient indicator value. The patient indicator value represents an answer to a question about the patient. The method further comprises performing a patient evaluation operation based on the patient indicator value.

In other illustrative embodiments, a computer program product comprising a computer usable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 5 shows an example query specification in accordance with an illustrative embodiment.

DETAILED DESCRIPTION

Figure 1:
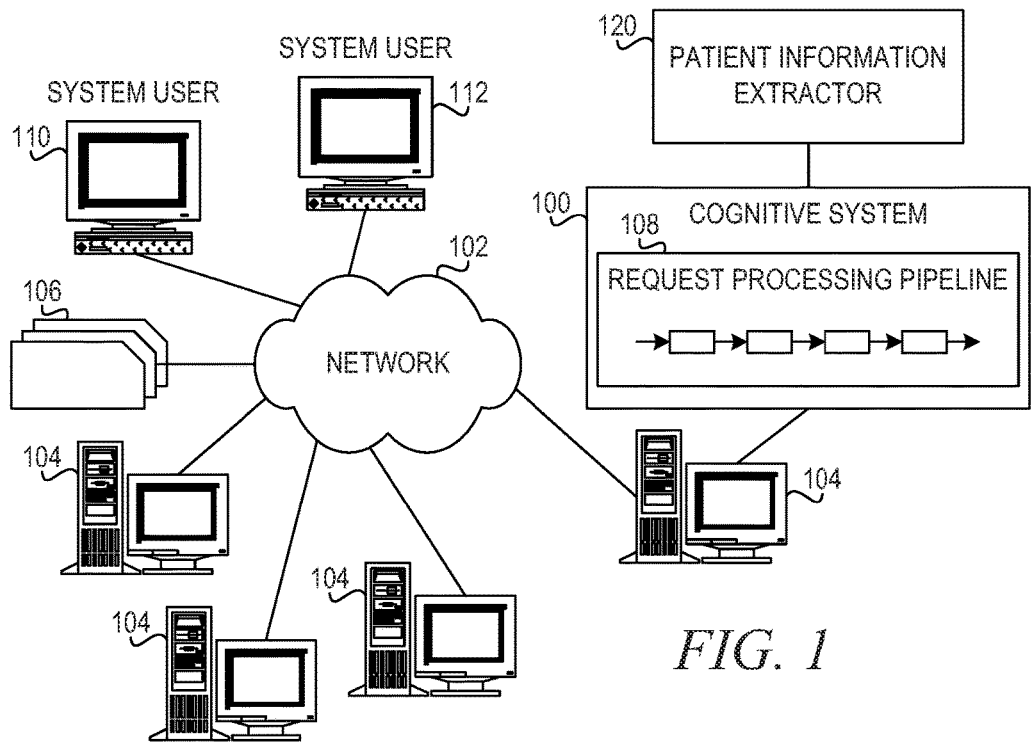
FIG. 1 depicts a schematic diagram of one illustrative embodiment of a cognitive system in a computer network.

In this disclosure, the term "patient indicator" refers to a value, which may be Boolean, numeric, date, categorical, or any other type, that represents the answer to a question about the patient, the patient's health, or the patient's medical, social, or family history present in an electronic medical record (EMR). Typical such questions include:

What is the patient's age?
What is the patient's ethnicity?
Does the patient have a family history of cancer?
Has the patient been on tamoxifen within the last year?
Did the patient ever have blood clots following surgery?
What kind of hysterectomy did the patient have?
When was the patient's last colonoscopy?

Several use cases require the gathering of collections of such indicators for one or many patients. These include retrospective chart review for clinical research, clinical trial matching (i.e., selecting suitable participants for a trial), quality assurance in health care systems, outcome prediction research, and epidemiology studies. Currently, these indicators are extracted from an EMR manually. This process is time-consuming, requires trained individuals, and is subject to human error. The illustrative embodiments provide an automatic mechanism for extracting patient indicators from an electronic medical record.

An indicator question falls into one of a small number of classes: yes/no, temporal, categorical, etc. The illustrative embodiments provide a dedicated search engine for each of these classes, which given one or more search terms and possible constraints can generate a list of search results. The illustrative embodiments also provide post-processors that take these search results and any constraints not expressible to the search engine, perform filtering and sorting, and extract indicator values.

All of the parameters for this search and extraction process can be laid out in a machine-readable attribute-value format, such as the JavaScript™ Object Notation (JSON), in a query specification data structure or document. The query specification contains entries for each indicator of interest. The process is as follows: the user writes a query specification for each patient indicator of interest; the query specification is run against the EMR, generating search results; the search results are post-processed to generate the indicator value; the indicator values are written out. This process may then be repeated for other patients, if desired. These indicators subsequently may be used to determine whether the patient qualifies for a trial, to predict likely future medical concerns, to assess whether appropriate care has been given, etc.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The illustrative embodiments may be utilized in many different types of data processing environments. In order to provide a context for the description of the specific elements and functionality of the illustrative embodiments, FIGS. 1-4 are provided hereafter as example environments in which aspects of the illustrative embodiments may be implemented. It should be appreciated that FIGS. 1-4 are only examples and are not intended to assert or imply any limitation with regard to the environments in which aspects or embodiments of the present invention may be implemented. Many modifications to the depicted environments may be made without departing from the spirit and scope of the present invention.

While the described embodiments describe a cognitive system, including a question-answering pipeline and an interactive session whereby users (doctors, technicians, healthcare workers, etc.) can query the system for information in order to help treat their patients, this is one possible use case scenario in which the illustrative embodiments may be employed; however, it is not necessarily the only or even the primary way in which the invention may be used. For instance, one application of the invention is for what is called clinical trial matching. A medical research team identifies a set of characteristics (such as middle-aged men, non-smokers, family history of heart problems, being treated for hypertension) for which they need to find a set of patients with these same characteristics for a follow-up study. In one illustrative embodiment, the medical research team would create the appropriate Query Specification which would be run against all of the EMRs they have available. This would create a result record for each patient, which can be scored to determine the degree of fit to their study needs. In this embodiment, there may be no interactive session and no (immediate) treatment of patients.

Another application of the invention is to aid the user in determining applicability of candidate treatments for a particular patient. The user identifies a set of patient-specific variables needed as evidential data to support or refute the applicability of a candidate treatment. Similar to the above example, the user would create the appropriate Query Specification to run against the specific EMR for the patient in question. The mechanism of this embodiment would return values for each user-specified variable, allowing the user to determine the most appropriate treatment option for the specific patient.

In accordance with yet another illustrative embodiment, which involves a question-answering (QA) pipeline (such as the IBM Watson™ cognitive system), logical search engines (LSEs), which take query terms from the query spec and produce hit lists, may include LSEs that accept query terms in the form of a natural language question. In this case, an LSE itself may be a QA system. Therefore, in this example embodiment, the QA system is called by the mechanisms of the illustrative embodiments.

FIGS. 1-4 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for providing medical treatment recommendations for patients based on their specific features as obtained from various sources, e.g., patient electronic medical records (EMRs), patient questionnaires, etc. In particular, the mechanisms of the present invention provide a mechanism for extracting patient information from an electronic medical record.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have its own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?" the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to providing a medical malady independent treatment recommendation system which may receive an input question regarding the recommended treatment for a specific patient and may utilize the QA pipeline mechanisms to evaluate patient information and other medical information in one or more corpora of medical information to determine the most appropriate treatment for the specific patient. Evaluation of the patient may be performed by the cognitive or by external mechanism proved by the system builder.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-4 are only examples and are not intended to state or imply any limitation with regard to the type of cognitive system mechanisms with which the illustrative embodiments are implemented. Many modifications to the example cognitive system shown in FIGS. 1-4 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

The IBM Watson™ cognitive system is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding

Ingest and process vast amounts of structured and unstructured data

Generate and evaluate hypothesis

Weigh and evaluate responses that are based only on relevant evidence

Provide situation-specific advice, insights, and guidance

Improve knowledge and learn with each iteration and interaction through machine learning processes Enable decision making at the point of impact (contextual guidance)

Scale in proportion to the task

Extend and magnify human expertise and cognition

Identify resonating, human-like attributes and traits from natural language

Deduce various language specific or agnostic attributes from natural language

High degree of relevant recollection from data points (images, text, voice) (memorization and recall)

Predict and sense with situational awareness that mimic human cognition based on experiences Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation that may be used in conjunction with the principles described herein is described in U.S. Patent Application Publication No. 2011/0125734, which is herein incorporated by reference in its entirety.

The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables question processing and answer generation (QA) functionality for one or more cognitive system users via their respective computing devices 110-112. Other embodiments of the cognitive system 100 may be used with components, systems, sub-systems, and/or devices other than those that are depicted herein.

The cognitive system 100 is configured to implement a QA pipeline 108 that receive inputs from various sources. For example, the cognitive system 100 receives input from the network 102, a corpus of electronic documents 106, cognitive system users, and/or other data and other possible sources of input. In one embodiment, some or all of the inputs to the cognitive system 100 are routed through the network 102. The various computing devices 104 on the network 102 include access points for content creators and QA system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of data 106 for use as part of a corpus of data with the cognitive system 100. The document includes any file, text, article, or source of data for use in the cognitive system 100. QA system users access the cognitive system 100 via a network connection or an Internet connection to the network 102, and input questions to the cognitive system 100 that are answered by the content in the corpus of data 106. In one embodiment, the questions are formed using natural language. The cognitive system 100 parses and interprets the question via a QA pipeline 108, and provides a response to the cognitive system user, e.g., cognitive system user 110, containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the QA pipeline 108 which comprises a plurality of stages for processing an input question and the corpus of data 106. The QA pipeline 108 generates answers for the input question based on the processing of the input question and the corpus of data 106. The QA pipeline 108 will be described in greater detail hereafter with regard to FIG. 4.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a QA pipeline of the IBM Watson™ cognitive system receives an input question which it then parses to extract the major features of the question, which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The QA pipeline of the IBM Watson™ cognitive system then performs deep analysis on the language of the input question and the language used in each of the portions of the corpus of data found during the application of the queries using a variety of reasoning algorithms.

The scores obtained from the various reasoning algorithms are then weighted against a statistical model that summarizes a level of confidence that the QA pipeline of the IBM Watson™ cognitive system has regarding the evidence that the potential response, i.e. candidate answer, is inferred by the question. This process is be repeated for each of the candidate answers to generate ranked listing of candidate answers which may then be presented to the user that submitted the input question, or from which a final answer is selected and presented to the user. More information about the QA pipeline of the IBM Watson™ cognitive system may be obtained, for example, from the IBM Corporation website, IBM Redbooks, and the like. For example, information about the QA pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a medical treatment recommendation system that analyzes a patient's EMR in relation to medical guidelines and other medical documentation in a corpus of information generate a recommendation as to how to treat a medical malady or medical condition of the patient.

In an illustrative embodiment, the cognitive system 100 implements a patient information extractor 120 for extracting patient information from a patient's EMR. A system user 110, 112 may provide a query specification (QS) for a specific indicator and an identification of one or more patient EMRs to patient information extractor 120, which runs the query specification against the EMR and generates search results. Patient information extractor 120 performs post-processing on the search results to generate the indicator value and returns the indicator value to the system user 110, 112.

Figure 6:
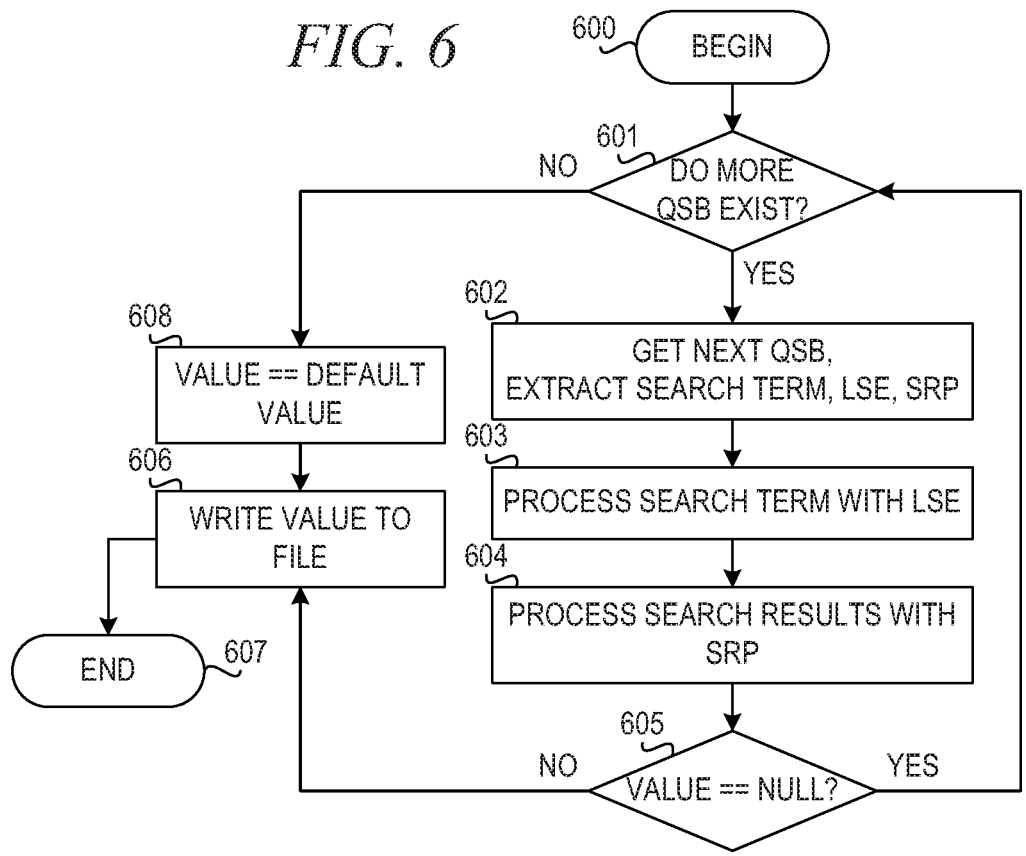
FIG. 6 is a flowchart illustrating operation of a patient information extractor in accordance with an illustrative embodiment.

In one embodiment, patient information extractor 120 provides one or more logical search engines (LSE), which find matches for search terms in the EMR according to specific logic, and one or more search result processors (SRP), which take the output of the LSEs, filter the results according to specified constraints, and return a result. Several LSEs may be implemented by the same physical search engine. The LSEs and SRPs are shown in FIG. 6 and described in further detail below.

Figure 2:
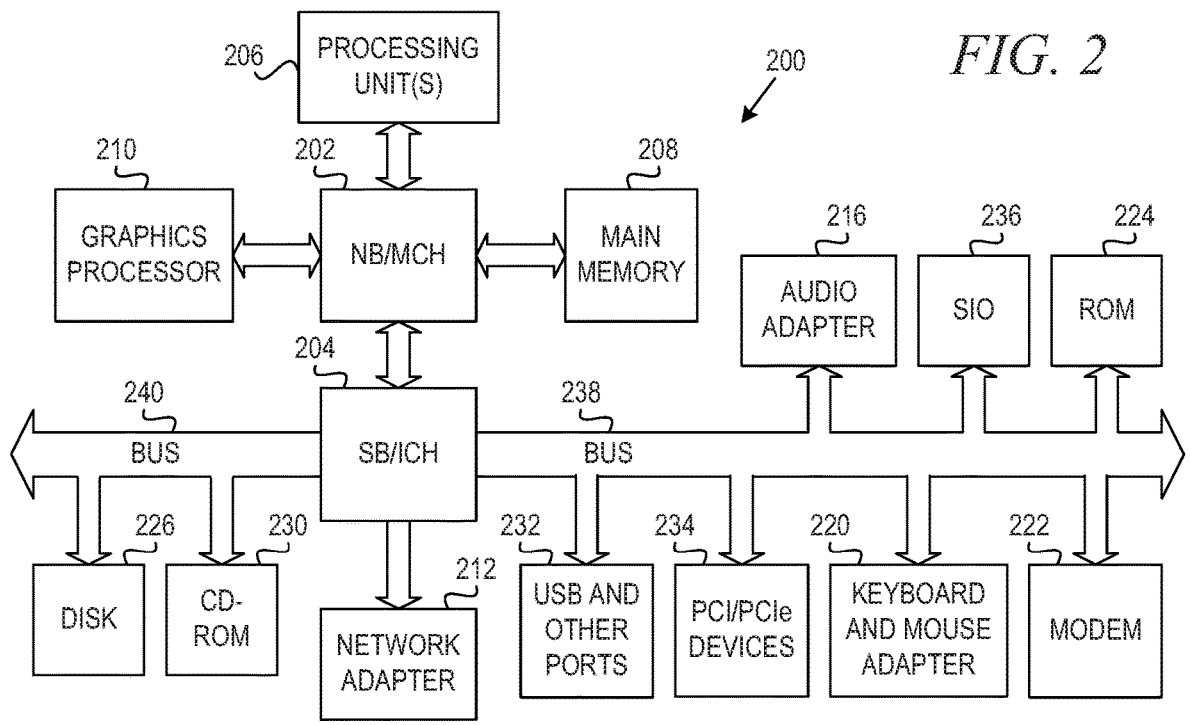
FIG. 2 is a block diagram of an example data processing system in which aspects of the illustrative embodiments are implemented.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements an NL processing system 100 and NL system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
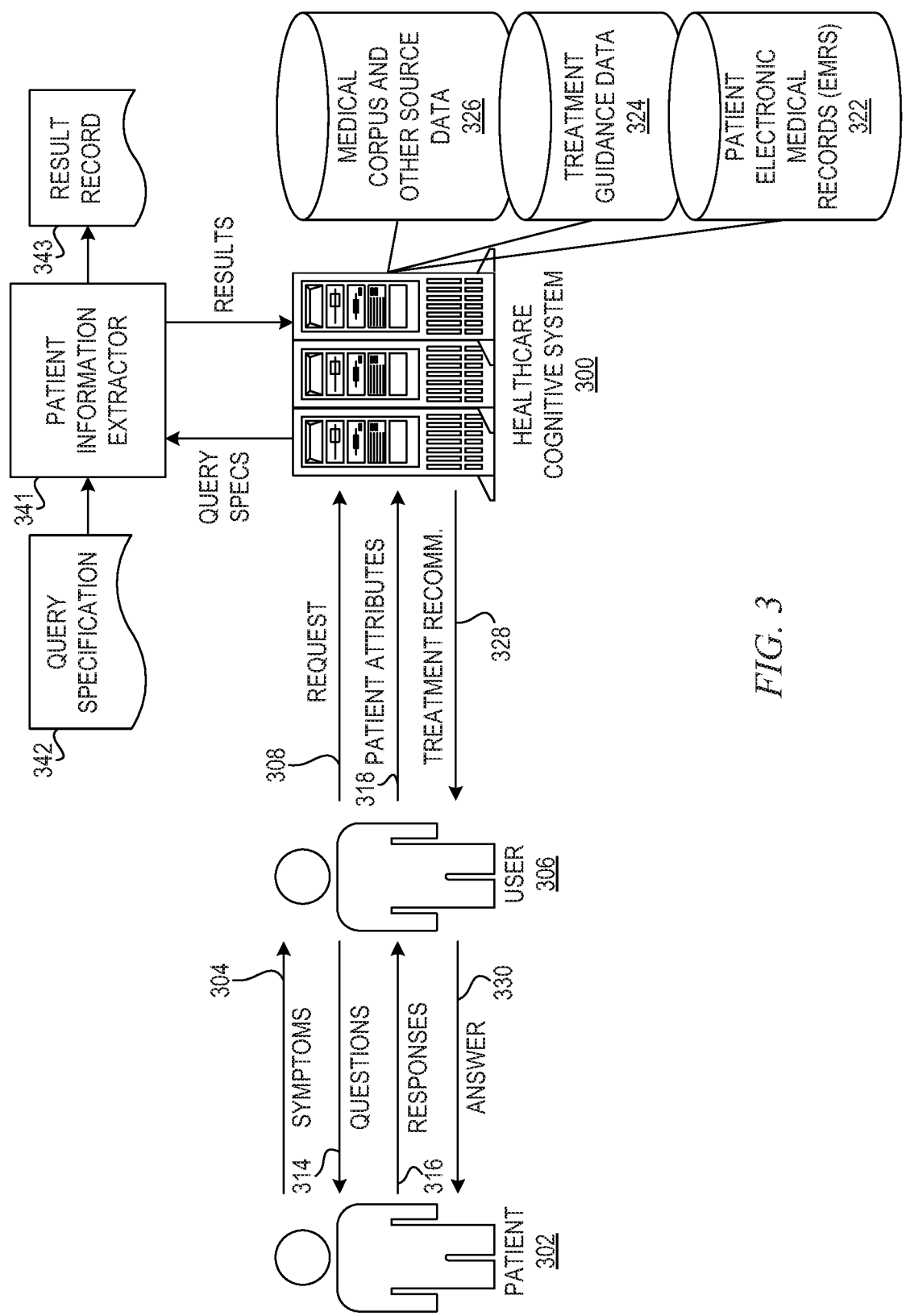
FIG. 3 is an example diagram illustrating an interaction of elements of a healthcare cognitive system in accordance with one illustrative embodiment.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. The user 306 may interact with the patient 302 via a question 314 and response 316 exchange where the user gathers more information about the patient 302, the symptoms 304, and the medical malady or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 302 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 to the user 306 to assist the user 306 in treating the patient 302 based on their reported symptoms 304 and other information gathered about the patient 302 via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate treatment recommendations (or answers to the input question), and score these candidate treatment recommendations based on supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326. While patient evaluation may be performed by cognitive system 300 itself, patient evaluation may also be performed by mechanisms outside cognitive system 300.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provide a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

In accordance with the illustrative embodiments herein, the healthcare cognitive system 300 is augmented to operate with, implement, or include patient information extractor 341 for extracting patient information from electronic medical records. User 306 may provide a query specification (QS) 342 for a specific indicator and an identification of one or more patient EMRs 322 to patient information extractor 341, which runs the query specification against the EMR and generates search results. Patient information extractor 341 performs post-processing on the search results to generate the indicator value and returns the indicator value in result record 343.

In one embodiment, patient information extractor 341 provides one or more logical search engines (LSE), which find matches for search terms in the EMR according to specific logic, and one or more search result processors (SRP), which take the output of the LSEs, filter the results according to specified constraints, and return a result. The LSEs and SRPs are shown in FIG. 6 and described in further detail below. The operation of patient information extractor 341 is described in further detail below with reference to FIGS. 5-7.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 treatment recommendations 328 from the healthcare cognitive system 300 directly based on the symptoms 304 provided by the patient 302 to the healthcare cognitive system 300. Moreover, the healthcare cognitive system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present invention.

As mentioned above, the healthcare cognitive system 300 may include a request processing pipeline, such as request processing pipeline 108 in FIG. 1, which may be implemented, in some illustrative embodiments, as a Question Answering (QA) pipeline. The QA pipeline may receive an input question, such as "what is the appropriate treatment for patient P?", or a request, such as "diagnose and provide a treatment recommendation for patient P."

Figure 4:
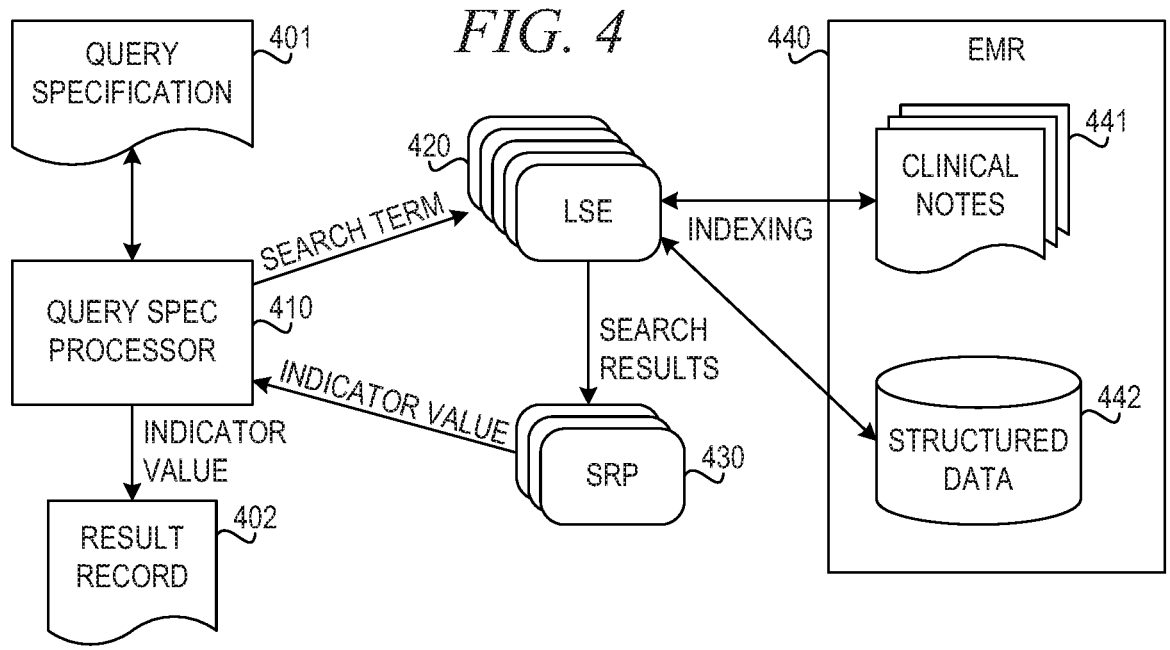
FIG. 4 is a block diagram of a patient information extractor in accordance with an illustrative embodiment.

FIG. 4 is a block diagram of a patient information extractor in accordance with an illustrative embodiment. Each patient is represented by an electronic medical record (EMR) 440. This record consists of (1) a number of clinical notes 441, which are free-text descriptions of patient encounters with medical staff (e.g., office visits), surgical procedures, and interactions between medical professionals concerning the patient, and (2) structured data 442 detailing ordered medications, tests and procedures, and patient demographic and possibly other static information (e.g., lists of allergies). It is likely and desirable, but not required for the purposes of this disclosure, that the EMR has been processed by analytic tools, such as MetaMap, which can detect free-text medical concepts and associate with them concepts in ontology, such as Unified Medical Language System (UM LS) dictionary, for example. The UMLS is a compendium of many controlled vocabularies in the biomedical sciences. It provides a mapping structure among these vocabularies and, thus, allows one to translate among the various terminology systems; it may also be viewed as a comprehensive thesaurus and ontology of biomedical concepts. UMLS further provides facilities for natural language processing. It is intended to be used mainly by developers of systems in medical informatics. Other useful but not required analytic tools would be tools that determine the type of clinical note (e.g., Office Visit, Operative Report, Telephone Encounter, Patient Instructions), and the sections within a note (e.g., Past Medical History, Current Medications, Assessment and Plan).

Query specification processor 410 receives a query specification (QS) 401. FIG. 5 shows an example query specification in accordance with an illustrative embodiment. The query specification (QS) for a specific indicator lists one or more query specification blocks (QSBs). Each QSB lists the search term(s) to be used, the LSE(s) to be used, a possible date restriction, a possible note type restriction, a possible section type restriction, a possible provider type restriction, a possible department/specialty restriction, the search result processor (SRP) to be used, and/or a mapping from search outputs to indicator outputs. In the example depicted in FIG. 5, the QS includes date restriction 501, QSBs 502, 503, 504, and note type 505. The QS specifies the LSE to use as "SemanticMatch," and specifies the SRP to use as "SpecificIndicator." QSB 502 searches for Bilateral salpingooophorectomy, QSB 503 searches for right or left salpingooophorectomy, and QSB 504 searches for no salpingooophorectomy (none). Note type 505 specifies to search the "operativenote," "ednote," "consultnote," and "procedurenote" note types in the EMR.

Returning to FIG. 4, query specification processor 410 is given the QS 401 for a given patient indicator and writes results to result record 402. In one embodiment, result record 402 may be a spreadsheet with one row per patient and one column per indicator variable. QS 401 consists of one or more QSBs, which are processed in order. If a particular QSB produces an outcome, it is written out and process stops for this indicator. Otherwise, the next QSB is processed. If no QSB produces an outcome, the null/default is written out.

In processing a QSB, query specification processor 410 calls the specified logical search engine (LSE) 420 with the specified search term. A "literal" LSE finds instances of the search term. For example, given a search term "heart attack," the LSE would match the term "heart attack." A "literal" LSE is similar to a standard find function and may or may not observe capitalization. A "semantic" LSE finds conceptual matches. For example, a "semantic" LSE may match the search term "heart attack" with the matched term "myocardial infarction," because both terms are mapped to the same concept in UMLS. A "more specific" LSE finds conceptual matches via "ISA" (is a) relations. In knowledge representation, object-oriented programming and design, "ISA" (is_a or is-a) is a subsumption relationship between abstractions (e.g., types, classes), where one class A is a subclass of another class B (and so B is a superclass of A). For example, a "more specific" LSE may match the search term "cancer" with "leukemia," because in UMLS, leukemia ISA cancer. An "associative" LSE finds terms that co-occur in external corpora. For example, an "associative" LSE may match the search term "asthma" with the matched term "wheezing." Standard technologies such as latent semantic analysis (LSA) do this. A "logical" LSE finds conceptual matches via relations other than ISA. For example, a "logical" LSE may match the search term "headache" with the matched term "Tylenol," because Tylenol® TREATS headache, and match the search term "Tylenol" to the matched term "acetaminophen," because Tylenol is a BRAND_NAME_OF acetaminophen.

Each LSE 420 should produce a list of results (possibly empty) with the following characteristics: the matched term, the date of the matched term (i.e., the date of the clinical note or structured entry containing the match), the confidence score of the match, the note type (if applicable) the matched term was found in, the section type (if applicable) the matched term was found in, the type of provider (e.g., physician, nurse, social worker) (if applicable) associated with the match, and/or the department/specialty (if applicable) associated with the match.

The LSE 420 searches EMR 440 and passes the search results to the specified search results processor (SRP) 430, along with any constraints. The SRP 430 takes in a hit list from the LSE 420 and a set of parameters. SRP 430 outputs an indicator value. Some parameters are common across SRPs, e.g., MinimumCount, which is the number of qualifying hit list entries that must be found for a positive result, and DateRange, which specifies a time window that qualifying hits must fall within.

A "SpecificIndicator" SRP receives an indicator value as a parameter and performs the following operation: If the hit list qualifies (by size and date range), return the indicator value, else null. A "YesNo" SRP performs the following operation: If the hit list qualifies, return Yes (or 1), else No (or 0). A "FirstLast" SRP receives a flag indicating First/Last as a parameter and performs the following operation: The qualifying hit list is sorted by date and the date of the first/last entry is returned. A "Temporal" SRP can receive as parameters one or two dates, each date with a flag indicating before/after. With this revision, the SRP can return yes/no depending on if the match falls within two specified dates. An "AnswerType" SRP receives an answer type indicating a property of the patient (e.g., age, weight) and performs the following operation: either the answer is looked up in the data structure part of the EMR, or a question-answering system is run on the clinical notes; the specified quantity is returned.

The SRP 430 filters the search results according to the constraints and returns a possible indicator value to the query specification processor 410. Query specification processor 410 writes the indicator value to result record 402.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

FIG. 6 is a flowchart illustrating operation of a patient information extractor in accordance with an illustrative embodiment. Operation begins for a current query specification and patient EMR (block 600), and the patient information extractor determines whether more query specification blocks (QSB) exist (block 601). Because a query specification has at least one QSB, the first iteration will result in a determination that more QSB exist. The patient information extractor then gets the next QSB in the query specification and extracts the specified search term, logical search engine (LSE), and search result processor (SRP) (block 602). The patient information extractor also extracts from the query specification one or more constraints, such as a date restriction, a note type restriction, a section type restriction, a provider type restriction, or a department/specialty restriction.

The patient information extractor processes the search term with the specified LSE to search the patient EMR and generate search results (block 603). The patient information extractor then processes the search results with the specified SRP to generate an indicator value (block 604). The patient information extractor determines whether the indicator value is null (i.e., the search results were empty or fail to meet the one or more constraints) (block 605). If the value is null, then the current QSB did not result in generating an indicator value, and operation returns to block 601 to determine whether more QSB exist. The patient information extractor then repeats blocks 602-605 for the next QSB if one exists.

If the patient information extractor determines that the indicator value is not null in block 605, then the current QSB generated a valid indicator value, and the patient information extractor writes the indicator value to a file (e.g., result record 402 in FIG. 4) (block 606). Thereafter, operation ends (block 607). Once a valid indicator value is found, operation ends for the current query specification. Operation may return to block 600 for a next query specification and the same or another patient EMR.

In response to the patient information extractor determining that the current QSB does not generate a valid indicator value in block 605 and that there are no more QSB (block 601: NO), operation proceeds to block 608 where the patient information extractor sets the indicator value to a default value. The patient information extractor then writes the indicator value to file (block 606), and operation ends (block 607). As stated above, operation may return to block 600 for a next query specification and the same or another patient EMR.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide a mechanism for extracting patient information from an electronic medical record. There are several current use cases that would benefit from extracting and collecting patient information from an EMR for further evaluation or analysis, including: clinical trial matching, retrospective chart review, outcome prediction, and quality assurance. Manual extraction of patient information from EMRs takes considerable time by trained individuals and is subject to human error. The mechanism of the illustrative embodiments uses automated extraction of patient indicators using a logical search engine on structured and unstructured data within a patient medical record. The illustrative embodiments is generalized to be applicable for all activities requiring data abstraction from patient medical records.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions which are executed by the at least one processor and configure the processor to implement a patient information extractor, wherein the method comprises:
   receiving, by the patient information extractor, a query specification for executing a query on a patient electronic medical record (EMR), wherein the query specification comprises a plurality of query specification blocks, wherein each query specification block specifies a search term, a logical search engine (LSE), and a search results processor (SRP);
   retrieving, by the patient information extractor, the patient EMR from a patient registry;
   automatically executing, by the patient information extractor, the query specification on the retrieved patient EMR to thereby extract the search results from the patient EMR in accordance with the parameters of the query specification, wherein automatically executing the query specification on the retrieved patient EMR comprises:
      processing the plurality of query specification blocks in order until a query specification block generates a valid patient indicator value, wherein processing a given query specification block comprises:
         executing its specified LSE to search the retrieved patient EMR to search for the specified search term and generate the search results, wherein the specified LSE produces a list of results including a matched term, a date of the matched term, a confidence score for the matched term, and a note type the matched term was found in; and
         executing its specified SRP to filter the search results according to specified constraints and return the patient indicator value, wherein the specified SRP receives the list of results and a set of parameters and returns an indicator value in accordance with the set of parameters; and
   performing a patient evaluation operation based on the patient indicator value.

2. The method of claim 1, wherein the specified LSE is selected from the group consisting of:
   a literal LSE that finds instances of the search term in the patient EMR;
   a semantic LSE that finds conceptual matches of the search term in the patient EMR;
   a conceptually more specific LSE that finds conceptual matches of the search tem in the patient EMR via ISA relations;
   an associative LSE that finds terms that co-occur in external corpora; and
   a logical LSE that finds conceptual matches via relations other than ISA.

3. The method of claim 1, wherein the specified SRP is selected from the group consisting on a SpecificIndicator SRP, a YesNo SRP, a FirstLast SRP, a Temporal SRP, and an AnswerType SRP.

4. The method of claim 1, wherein the patient evaluation operation is one of a retrospective patient medical chart review operation for clinical research, a clinical trial matching operation, a quality assurance operation for a health care system, a medical outcome prediction operation, or an epidemiology studies operation.

5. The method of claim 1, wherein the patient indicator value is one of a Boolean value, a numeric value, a temporal value, or a categorical value.

6. The method of claim 1, wherein the patient EMR comprises unstructured natural language content and structured information content detailing at least one of encounters with a corresponding patient, procedures performed on the patient, interactions with medical practitioners concerning the patient, medications associated with the patient, results of medical tests and procedures, patient demographic information, or static medical condition information.

7. Me method of claim 6, wherein automatically executing the query specification on the patient EMR comprises performing natural language processing operations on the unstructured natural language content to extract the search results in accordance with the parameters specified in the query specification.

8. The method of claim 1, wherein automatically executing the query specification on the patient EMR comprises utilizing one or more logical search engines to extract the search results, wherein the search results of the one or more logical search engines comprises at least one matched natural language term, and wherein for each matched natural language term in the at least one matched natural language term, at least one of:
   a date associated with matched natural language term;
   a confidence score associated with the matched natural language term;

a type of clinical note in which the matched natural language term was found;
a type of section of the patient EMR in which the matched natural language term was found;
a type of medical practitioner that, is a source matched natural language term in the patient EMR; or
a medical department or medical, specialty associated with the matched natural language term.

9. The method of claim 1, wherein the parameters specified in the query specification comprise at least one parameter selected from the following:
natural language terms to be searched for in a natural language search operation;
specific logical search engines in a plurality of logical search engines to utilize to execute the query specification on a patient EMR;
a date restriction for the search results;
a clinical note type restriction for the search results;
a patient EMR section type restriction for the search results;
a medical practitioner source restriction for the search results;
a medical department or medical specialty type restriction for the search results;
a specific search result processor in a plurality of search result processors, each of which generates a different type of patient indicator value, for generating the patient indicator value based on the search results; or
a mapping from the search results to the patient indicator value.

10. A computer program product comprising a computer readable swage medium having a computer readable program stored therein, wherein the computer readable program comprises instructions, which when executed on a processor of a computing device causes the computing device to implement a patient information extractor, wherein the computer readable program causes the computing device to:
receive, by the patient information extractor, a query specification for executing a query on a patient electronic medical record (EMR), wherein the query specification comprises a plurality of query specification blocks, wherein each query specification block specifies a search term, a logical search engine (LSE), and a search results processor (SRP);
retrieve, by the patient information extractor, the patient EMR from a patient registry;
automatically execute, by the patient information extractor, the query specification on the retrieved patient EMR to thereby extract the search results from the patient EMR in accordance with the parameters of the query specification, wherein automatically executing the query specification on the retrieved patient EMR comprises:
processing the plurality of query specification blocks in order until a query specification block generates a valid patient indicator value, wherein processing a give query specification block comprises:
executing its specified LSE to search the retrieved patient EMR to search for the specified search term and generate the search results, wherein the specified LSE produces a list of results including a matched term, a date of the matched term, a confidence score for the matched term, and a note type the matched term was found in; and
executing its specified SRP to filter the search results according to specified its specified SRP to filter the search results according to specified constraints and return the patient indicator value, wherein the specified SRP receives the list of results and a set of parameters and returns an indicator value in accordance with the set of parameters; and
perform a patient evaluation operation based on the patient indicator value.

11. The computer, program product of claim 10, wherein the patient EMR comprises unstructured natural language content and structured information content detailing at least one of encounters with a corresponding patient, procedures performed on the patient, interactions with medical practitioners concerning the patient, medications associated with the patient, results of medical tests and procedures patient demographic information, or static medical condition information.

12. The computer program product of claim 10, wherein the specified LSE is selected from the group consisting of:
a literal LSE that finds instances of the search term in the patient EMR;
a semantic LSE that, finds conceptual matches of the search term in the patient EMR;
a conceptually more specific LSE that finds conceptual matches of e search term in the patient EMR via ISA relations;
an associative LSE that finds terms that co-occur in external corpora; and
a logical LSE that finds conceptual matches via relations other than ISA.

13. The computer program product of claim 10, wherein the specified SRP is selected from the group consisting of a SpecificIndicator SRP, a YesNo SRP, a FirstLast SRP, a Temporal SRP, and an AnswerType SRP.

14. The computer program product of claim 10, wherein automatically executing the query specification on the patient EMR comprises utilizing one or more logical search engines to extract the search results, wherein the search results of the one or more logical search engines comprises at least one matched natural language term, and wherein for each matched natural language term in the at least one matched natural language term, at least one of:
a date associated with matched natural language term;
a confidence score associated with the matched natural language term;
a type of clinical note in which the matched natural language term was found;
a type of section of the patient EMR in which the matched natural language term was found;
a type of medical practitioner that is a source of the matched natural language term in the patient EMR; or
a medical department or medical specialty associated with the matched natural language term.

15. The computer program product of claim 10, wherein the parameters specified in the query specification comprise at least one parameter sled from the following:
natural language terms to be searched for in a natural language search operation;
specific logical search engines in a plurality of logical search engines to utilize to execute the query specification on a patient EMR;
a date restriction for the search results;
a clinical note type restriction for the search results;
a patient EMR section type restriction for the search results;
a medical practitioner source restriction for the search results;
a medical department or medical specialty type restriction for the search results;

a specific search result processor in a plurality of search result processors, each of which generates a different type of patient indicator value, for generating the patient indicator value based on the search results; or
a mapping from the search results to the patient indicator value.

16. A computing device comprising:
a processor; and
a memory coupled to the processor, wherein the memory comprises instructions, which when executed on a processor of a computing device causes the computing device to implement a patient information extractor, wherein the instructions cause the processor to:
receive, by the patient information extractor, a query specification for executing a query on a patient electronic medical record (EMR), wherein the query specification comprises a plurality of query specification blocks, wherein each query specification block specifies a search term, a logical search engine (LSE), and, a search results processor (SRP);
retrieve, by the patient information extractor, the patient EMR patient registry;
automatically execute, by the patient information extractor, the query specification on the retrieved patient EMR to thereby extract the search results from the patient EMR in accordance with the parameters of the query specification, wherein automatically executing the query specification on the retrieved patient EMR comprises:
processing the plurality of query specification blocks in order until a query specification block generates a valid patient indicator value, wherein processing a given query specification block comprises:
executing its specified LSE to search the retrieved patient EMR to search for the specified search term and generate the search results, wherein the specified LSE produces a list of results including a matched term, a date of the matched term, a confidence score for the matched term, and a note type the matched term was found in; and
executing its specified SRP to filter the search results according to specified constraints and return the patient indicator value, wherein the specified SRP receives the list of results, and a set of parameter and returns an indicator value in accordance with the set of parameters; and
perform a patient evaluation operation based on the patient indicator value.

17. The computing device of claim 16, wherein the patient EMR comprises unstructured natural language content and structured information content detailing at least one of encounters with a corresponding patient, procedures performed on the patient, interactions with medical practitioners concerning the patient, medications associated with the patient, results of medical tests and procedures, patient demographic information, or static medical condition information.

18. The computing device of claim 16, wherein the specified LSE is selected from the group consisting of:
a literal LSE that finds instances of the search term in the patient EMR;
a semantic LSE that finds conceptual matches of the search term in the patient EMR;
a conceptually more specific LSE that finds conceptual matches of the search term in the patient EMR via ISA relations;
an associative LSE that finds terms that co-occur in external corpora; and
a logical LSE that finds conceptual matches via relations other than ISA.

19. The computing device of claim 16, wherein the specified SRP is selected from the group consisting of: a SpecificIndicator SRP, a YesNo SRP, a FirstLast SRP, a Temporal SRP, and an AnswerType SRP.

20. The computing device of claim 16, wherein automatically executing the query specification on the patient EMR comprises utilizing one or more logical search engines to extract the search results, wherein the search results of the one or more logical search engines comprises at least one matched natural language term, and wherein for each matched natural language term in the at least one matched natural language term, at least one of:
a date associated with matched natural language term;
a confidence score associated with the matched natural language term;
a type of clinical note in which the matched natural language term was found;
a type of section of the patient EMR in which the matched natural language term was found;
a type of medical practitioner that is a source of the matched natural language term in the patient EMR; or
a medical department or medical specialty associated with the matched natural language term.

* * * * *